(12) United States Patent
Matthews et al.

(10) Patent No.: US 6,961,601 B2
(45) Date of Patent: Nov. 1, 2005

(54) SENSOR SYSTEM FOR MEASURING BIOPOTENTIALS

(75) Inventors: Robert Matthews, San Diego, CA (US); Michael A. Krupka, San Diego, CA (US); Andrew D. Hibbs, La Jolla, CA (US)

(73) Assignee: Quantum Applied Science & Research, Inc., San Diego, CA (US)

( * ) Notice: Subject to any disclaimer, the term of this patent is extended or adjusted under 35 U.S.C. 154(b) by 222 days.

(21) Appl. No.: 10/459,267

(22) Filed: Jun. 11, 2003

(65) Prior Publication Data

US 2004/0254435 A1 Dec. 16, 2004

(51) Int. Cl.⁷ .............................................. A61B 5/04
(52) U.S. Cl. ...................... 600/372; 600/386
(58) Field of Search ................ 600/372, 373, 600/386

(56) References Cited

U.S. PATENT DOCUMENTS

| | | | |
|---|---|---|---|
| 3,500,823 A * | 3/1970 | Richardson et al. ........ | 600/372 |
| 3,565,060 A * | 2/1971 | Sipple ....................... | 600/508 |
| 3,620,208 A * | 11/1971 | Higley et al. ............... | 600/395 |
| 3,722,677 A | 3/1973 | Lehnert | |
| 3,744,482 A | 7/1973 | Kaufman et al. | |
| 3,815,000 A | 6/1974 | Phillips | |
| 3,880,146 A | 4/1975 | Everett et al. | |
| 3,882,846 A * | 5/1975 | Fletcher et al. ............. | 600/395 |
| 3,923,042 A | 12/1975 | Hajdu et al. | |
| 4,248,244 A | 2/1981 | Charnitski et al. | |
| 4,580,576 A | 4/1986 | Blackwood | |
| 4,581,821 A | 4/1986 | Cahalan et al. | |
| 4,602,639 A | 7/1986 | Hoogendoorn et al. | |
| 4,669,479 A | 6/1987 | Dunseath, Jr. | |
| 4,688,141 A | 8/1987 | Bernard et al. | |
| 4,785,237 A | 11/1988 | Cox | |
| 4,801,866 A | 1/1989 | Wixley | |
| 5,001,594 A | 3/1991 | Bobbio | |
| 5,015,906 A | 5/1991 | Cho et al. | |

(Continued)

FOREIGN PATENT DOCUMENTS

CA        2428250        11/2003

(Continued)

OTHER PUBLICATIONS

Harland et al., "Remote Detection of Human Electroencephalograms Using Ultrahigh Input Impedance Electric Potential Sensors", Applied Physics Letter, pp. 3284-3286, vol. 81, No. 17, 2002.

(Continued)

*Primary Examiner*—Lee S. Cohen
(74) *Attorney, Agent, or Firm*—Diederiks & Whitelaw, PLC

(57) ABSTRACT

A system for measuring a biopotential signal produced by a body in free space at a location adjacent to the body, and if desired, through clothing, includes a probe that can be positioned adjacent to the body. The probe includes a conductive electrode to receive the biopotential signal and a conductor that is maintained at a fixed distance from the electrode. The potential of the conductor can be maintained substantially equal to the potential of the electrode to shield the electrode from stray electrical noise. The system further includes a high impedance first stage amplifier that is incorporated into the probe and electrically connected to the electrode using a relatively short connector to minimize connector noise. Functionally, the first stage amplifier compares the electrical potential of the electrode to a second potential (e.g. a local ground) and generates a signal that is indicative of the biopotential.

40 Claims, 3 Drawing Sheets

U.S. PATENT DOCUMENTS

| | | | |
|---|---|---|---|
| 5,039,312 | A | 8/1991 | Hollis, Jr. et al. |
| 5,090,643 | A | 2/1992 | Spears |
| 5,119,404 | A | 6/1992 | Aihara |
| 5,191,891 | A | 3/1993 | Righter |
| 5,229,593 | A | 7/1993 | Cato |
| 5,289,822 | A | 3/1994 | Highe et al. |
| 5,304,941 | A | 4/1994 | Tateishi |
| 5,325,073 | A | 6/1994 | Hasegawa |
| 5,336,999 | A | 8/1994 | Mansfield et al. |
| 5,485,092 | A | 1/1996 | Fortin |
| 5,488,677 | A | 1/1996 | Tokano |
| 5,574,805 | A | 11/1996 | Toba et al. |
| 5,632,280 | A | 5/1997 | Leyde et al. |
| 5,645,527 | A | 7/1997 | Beck |
| 5,650,750 | A | 7/1997 | Leyde et al. |
| 5,670,870 | A | 9/1997 | Muramatsu |
| 5,699,015 | A | 12/1997 | Dotson et al. |
| 5,734,296 | A | 3/1998 | Dotson et al. |
| 5,751,192 | A | 5/1998 | Main |
| 5,781,003 | A | 7/1998 | Kondo |
| 5,795,293 | A | 8/1998 | Carim et al. |
| 5,798,673 | A | 8/1998 | Griffith et al. |
| 5,896,035 | A | 4/1999 | Takahashi |
| 5,947,920 | A | 9/1999 | Beck |
| 6,096,220 | A | 8/2000 | Ohkawa |
| 6,111,466 | A | 8/2000 | Mokhtar et al. |
| 6,134,424 | A | 10/2000 | Nishihori et al. |
| 6,242,911 | B1 | 6/2001 | Maschek |
| 6,262,631 | B1 | 7/2001 | Li |
| 6,411,108 | B1 | 6/2002 | Douglas et al. |
| 6,438,413 | B1 | 8/2002 | Taheri |
| 6,472,888 | B2 | 10/2002 | Oguma et al. |
| 6,551,252 | B2 | 4/2003 | Sackner et al. |
| 6,611,168 | B1 | 8/2003 | Denison et al. |
| 6,686,800 | B2 | 2/2004 | Krupka |
| 6,755,795 | B2 | 6/2004 | Marmaropoulos et al. |
| 6,807,438 | B1 * | 10/2004 | Brun Del Re et al. ...... 600/372 |
| 2002/0038092 | A1 | 3/2002 | Stanaland et al. |
| 2003/0036691 | A1 | 2/2003 | Stanaland et al. |
| 2003/0214408 | A1 | 11/2003 | Grajales et al. |
| 2004/0070446 | A1 | 4/2004 | Krupka |
| 2004/0073104 | A1 * | 4/2004 | Brun del Re et al. ...... 600/372 |

FOREIGN PATENT DOCUMENTS

| | | |
|---|---|---|
| WO | WO 01/16607 | 3/2001 |
| WO | WO 02/065905 | 8/2002 |
| WO | WO 03/048789 | 6/2003 |
| WO | WO 03/079897 | 10/2003 |

OTHER PUBLICATIONS

Harland et al., "Electric Potential Probes—New Directions in the Remote Sensing of the Human Body", Measuring Science and Technology, pp. 163-169, No. 13, 2002.

Byrne et al., Ground-Based Instrumentation for Measurements of Atmospheric Conduction Current and Electric Field at the South Pole, pp. 2611-2618, Journal of Geophysical Research, vol. 98, No. D2, Feb. 20, 1993.

Clippingdale et al., Ultrahigh Impedance Capacitively Coupled Heart Imaging Array, pp. 269-270, Rev. Sci. Instrum. 65 (1), Jan. 1994.

Harrison, An Antenna Electrometer System for Atmospheric Electrical Measurements, pp. 1599-1603, Rev. Sci. Instrum. 68 (3), Mar. 1997.

Maynard, Electric Field Measurements in Moderate to High Density Space Plasmas with Passive Double Probes, pp. 13-27, Geophysical Monograph 103, American Geophysical Union 1998.

Pedersen, Electric Field Measurements in a Tenuous Plasma with Spherical Double Probes, pp. 1-12, Geophysical Monograph 103, American Geophysical Union 1998.

Prance et al., An Ultra-Low-Noise Electrical-Potential Probe for Human-Body Scanning, pp. 1-7, Meas. Sci. Technol. 11 (2000).

Author Unknown, "Ultra Low Input Bias Current Instrumentation Amplifier", Burr-Brown Corp. pp. 1-9, 1994.

Clippingdale et al., "Ultrahigh Impedance Voltage Probes and Non-Contact Electrocardiography," Sensors: Technology Systems and Applications, IOP Publ. Ltd., 1$^{st}$ Edition, pp. 469-472, 1991.

Clippingdale et al., "Non-Invasive Dielectric Measurements with the Scanning Potential Microscope," J. Phys. D: Appl. Phys., IOP Publ. Ltd., vol. 27, pp. 2426-2430, 1994.

David et al., "Insulated Electrocardiogram Electrodes," Med. & Biol. Eng., Peter Peregrinus Ltd., vol. 10, pp. 742-750, 1972.

Geddes, L.A., "Electrodes and the Measurement of Bioelectric Events," Wiley-Interscience, pp. 97-106, 1972.

Harland et al., "High Resolution Ambulatory Electrocardiographic Monitoring Using Wrist-Mounted Electric Potential Sensors," Meas. Sci. and Technol., IOP Publ. Ltd., vol. 14, pp. 923-928, 2003.

Horowitz et al., "The Art of Electronics," 2$^{nd}$ Edition, pp. 96-98, 183-187, 193-207, 209-210, 1989.

Nunez, P. L., "Electric Fields of the Brain: The Neurophysics of EEG," Oxford U. Press, pp. 197-198, 1981.

Nunez, P.L. et al., "Spatial-Temporal Structures of Human Alpha Rhythms: Theory, Microcurrent Sources, Multiscale Measurements, and Global Binding of Local Networks," Human Brain Mapping, Wiley-Liss, Inc., vol. 13, pp. 125-164, 2001.

Prance et al., "Electrometer Arrays: Sensing of Spatio-Temporal ELF Fields," Proc. Marelec, 3.4, 1997.

Prance et al., "Non-Contact VLSI Imaging Using a Scanning Electric Potential Microscope," Meas. Sci. and Technol. vol. 9, pp. 1229-1235, 1998.

Richardson, P.C., "The Insulated Electrode: A Pasteless Electrocardiographic Technique," 20$^{th}$ Annual Conference on Engineering in Medicine and Biology, pp. 15.7, Nov. 1967.

Srebo, R., "Localization of Visually Evoked Cortical Activity in Humans," J. Physiology, vol. 360, pp. 233-246, 1985.

Srinivasan et al., "Spatial Sampling and Filtering of EEG with Spline Laplacians to Estimate Cortical Potentials," Brain Topography, Human Sciences Press, Inc., vol. 8, No. 4, pp. 355-366, 1996.

* cited by examiner

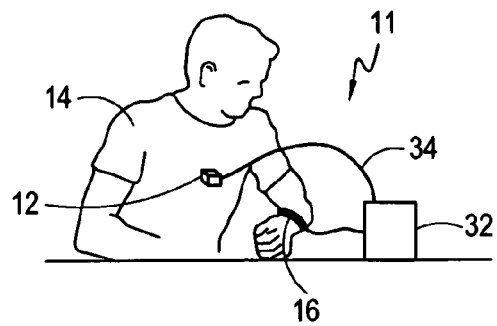
Fig. 1
Fig. 2
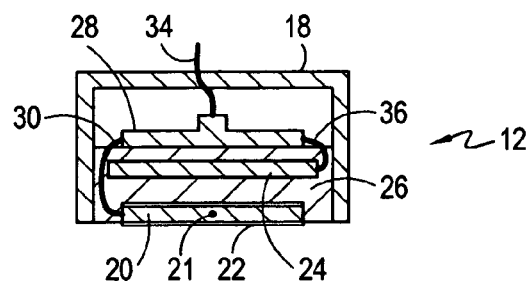
Fig. 3
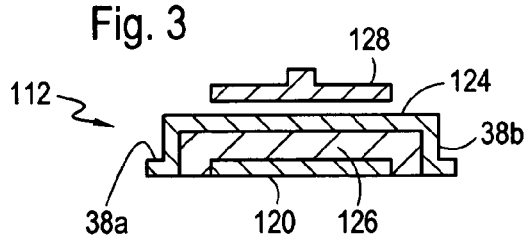
Fig. 4
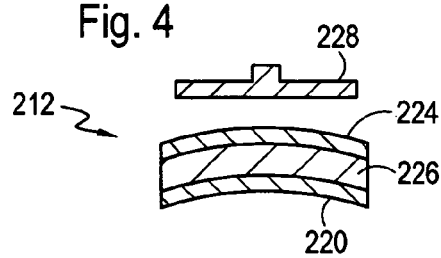
Fig. 5
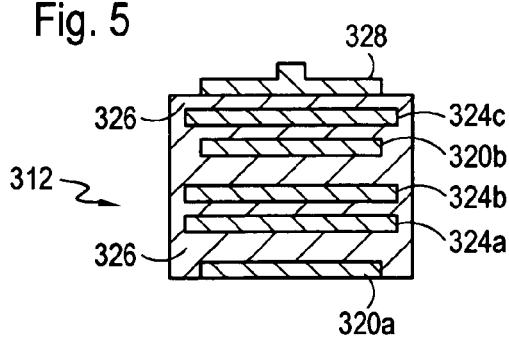

SENSOR SYSTEM FOR MEASURING BIOPOTENTIALS

FIELD OF THE INVENTION

The present invention pertains generally to systems for measuring biopotentials. More particularly, the present invention pertains to systems for non-invasively measuring biopotential signals emanating from a specific portion of a patient's body. The present invention is particularly, but not exclusively, useful for measuring biopotentials through a patient's clothing.

BACKGROUND OF THE INVENTION

There are many current and emerging technologies, including medical procedures, that benefit from the measurement of biopotentials. One of the most common procedures using biopotential measurement is probably the electrocardiogram (EKG), which is typically used to assess heart rhythms. While the capabilities of almost all aspects of the systems used to implement these measurements continue to improve, the somewhat limited performance of biopotential sensors has limited the applications in which biopotential measurement can be successfully performed.

With this in mind, biopotential sensors can generally be categorized as either invasive or non-invasive. Invasive sensors are typically implanted surgically and are generally used to isolate one or more specific potential sources such as the brain or the peripheral nervous system. Non-invasive sensors, on the other hand, have heretofore been applied to a surface such as the patient's skin or scalp. One type of non-invasive sensor, often referred to as a wet electrode, utilizes a conducting electrolyte, typically a gel, to electrically connect the electrode to the skin of the patient. This technique is currently the standard method used in clinical and research applications due to the relatively low cost of the electrode, its relatively long history of use, and the fact that the technique achieves a relatively good electrical contact between the electrode and the patient. There are, however, certain disadvantages with this technique. For some applications (e.g. an EKG), the technique requires the patient to disrobe and may require the skin to be shaved and prepped. Because of these requirements, procedures using wet electrodes are often time consuming, labor intensive and uncomfortable for the patient.

Another type of non-invasive sensor utilizes a surface electrode that does not require an electrolyte gel. These electrodes are referred to as active electrodes and typically employ an impedance transformation using active electronics. The active electrodes can be either insulated electrodes or dry electrodes (i.e. non-insulated). Typically, the active dry electrode is a conductive metal which is placed in direct contact with the skin and relies on a combination of resistive and capacitive coupling to the local skin potential to receive its signal. On the other hand, the insulated electrode relies entirely on capacitive coupling for this purpose.

Heretofore, active dry and insulated electrodes have not typically exhibited the same consistency and signal to noise ratio (SNR) as wet electrodes. Although considerable efforts have been made to improve insulated electrodes by using coatings with a high dielectric constant to improve the capacitance to the skin, there are still substantial limitations associated with currently available non-invasive sensors, including those that use insulated electrodes. For example, currently available sensors are strongly affected by small displacements away from the skin. In greater detail, as implied above, these sensors must be positioned either directly in contact with, or extremely close to, the skin. For dry electrodes, the signal is completely lost if the electrode is moved away from the skin by only a few microns. For capacitive electrodes, the effect of electrode displacement can be estimated by first recognizing that the capacitive coupling is similar to that of a parallel plate capacitor in which the skin acts as one capacitor plate and the electrode acts as the other plate. Based on this model, the coupling is proportional to the inverse of the separation distance between the sensor and the skin. In numerical terms, the coupling is typically reduced by a factor of about 10 as the electrode moves from a position of contact with the skin to a stand-off distance of only about 100 $\mu$m.

Heretofore, efforts to reduce the effects of small sensor displacements have involved using capacitive sensors with multiple sensing regions. Relatively complicated processing circuitry is then integrated with the active electronics connected to the electrode to switch between signals from sensing regions having adequate electrode coupling and signals from sensing regions where the electrode coupling is insufficient. While in theory this approach can reduce the effect of sensor motion in the final measurement, it has not been widely adopted.

In contrast to the above-described techniques, the present invention contemplates a sensor capable of measuring an electric potential in free space. More specifically, the present invention contemplates the measurement of an electric potential with an electrode that is not necessarily in direct contact with, or even extremely close to, the biopotential source. Unlike the sensors described above, for an electrode that is spaced from the biopotential source, the effect of a small displacement between the sensor and biopotential source is minimal. In greater detail, it is known that the electric potential, E, produced in a uniform medium by a simple source of electrical potential such as a charge decreases in accordance with the relationship, $E \propto 1/\text{distance}^2$. Thus, for a sensor having an electrode spaced at a distance of 2 cm from a dipole source, the relative change in signal for a 100 $\mu$m displacement away from the source is only about 1%.

Unfortunately, the measurement of the free-space electric potential (i.e. measurement with an electrode that is not necessarily in direct contact with, or extremely close to the biopotential source) cannot be performed effectively with currently available sensors. Specifically, conventional insulated electrodes typically rely on a relatively large mutual capacitance between the electrode sensing area and the surface of the skin. For an electrode pressed directly on the skin, the resulting capacitance can be as high as 0.1 $\mu$F/cm$^2$. With this relatively large capacitance, it is relatively simple to construct an amplifier using modern semiconductor technology with sufficiently high input impedance and input bias current path impedance to effectively amplify the signal from such an electrode. However, to measure a potential in free space, one is limited to the free space capacitance of the sensing part of the electrode. This capacitance is typically about 1 pF multiplied by the average radius of the electrode measured in centimeters, thus the capacitance is only about 1 pF for most practical applications.

Typically, to measure the free space potential with an adequate sensitivity for most biopotential measurement applications, it is preferable that the sensor electrode measure the free space electric potential with a noise floor of below approximately 20 $\mu$V/Hz$^{0.5}$ at 1 Hz. Further, to achieve a voltage noise of about 20 $\mu$V/Hz$^{0.5}$ at 1 Hz requires an input current noise on the order of about 1 fA/Hz$^{0.5}$ at 1

Hz. In addition, coupling to the small free space capacitance of the sensor electrode (i.e. 1 pF) generally requires that the input impedance of the first stage sensor electronics be of the same order as the impedance of the sensing layer. This translates to an input resistance of about 100 G$\Omega$ or higher, and an input capacitance of about 10 pF or less. Also, the circuit used to provide the input bias current to the first stage electronics should have an impedance to ground of the same order as the amplifier input impedance, and stray capacitances at the input to the system should be less than the amplifier input capacitance. These specifications delineate a threshold sensitivity for measuring a typical biopotential at a standoff distance. To measure smaller than average biopotential signals, such as those that arise in an electroencephalogram (EEG), it is desirable that the amplifier input impedance be even higher, and the first stage amplifier current noise be even lower.

In light of the above, it is an object of the present invention to provide systems and methods suitable for effectively measuring a biopotential signal that are operable with a relatively weak coupling between the sensor electrode and the biopotential source. It is yet another object of the present invention to provide systems and methods for measuring biopotentials that minimize the effect of small movements between the sensor electrode and the biopotential source during measurement. It is another object of the present invention to provide systems and methods for non-invasively measuring biopotential signals through a patient's clothing. Yet another object of the present invention is to provide systems and methods for measuring biopotentials which are easy to use, relatively simple to implement, and comparatively cost effective.

SUMMARY OF THE INVENTION

The present invention is directed to systems and methods for measuring a biopotential signal at a location adjacent to a patient. In one application, the system can be used to measure a biopotential signal through a patient's clothing. For the present invention, the system includes a probe that can be positioned adjacent to the patient. The probe includes an electrode that is made of a conductive material, such as a metal, to receive the biopotential signal. Typically, the surface of the electrode is covered with a resistive coating to shield the electrode from stray electrical currents.

The probe further includes a conductor that is spaced at a distance from the electrode. Typically, a material having a relatively low conductivity and dielectric constant is interposed between the conductor and the electrode to prevent electrical interaction between the conductor and electrode. As detailed further below, in one embodiment of the present invention, the potential of the conductor is controlled to be substantially equal to the potential of the electrode to effectively shield the electrode from electrical noise. Thus, in this embodiment, the conductor functions as a guard for the electrode.

The system further includes a high impedance first stage amplifier that is incorporated into the probe and electrically connected to the electrode. With the first stage amplifier located proximate the electrode, a relatively short connector can be used which admits less noise into the system than would otherwise be admitted by a relatively long connector. For the present invention, the high impedance first stage amplifier can be constructed from an instrumentation amplifier, an operational amplifier or from discrete transistors. Functionally, the first stage amplifier compares the electrical potential of the electrode to a second potential (described further below) and generates a signal in response. The system can further include second stage electronics to receive the signal generated by the high impedance first stage amplifier. Typically, the second stage electronics are remotely positioned from the probe and can be configured to selectively filter, amplify, store and display the signal generated by the high impedance first stage amplifier.

In one embodiment of the system, the reference potential of the patient is used as the second potential (i.e. the potential that is compared to the electrical potential at the electrode). In this embodiment, a reference electrode can be electrically connected to the patient to transmit the second potential to the high impedance first stage amplifier. In another embodiment, the probe includes a second electrode that is spaced from the first electrode (i.e. the electrode described above). The second electrode is exposed to a second potential which is input to the high impedance first stage amplifier for comparison with the first potential. In yet another embodiment, the electrical potential of the electrode is compared to a local ground at the high impedance first stage amplifier to measure the biopotential signal.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a perspective view of a system for measuring a biopotential signal shown operationally positioned to measure a biopotential signal of a patient;

FIG. 2 is a cross sectional view of a probe for use in the system shown in FIG. 1;

FIG. 3 is a cross sectional view of another embodiment of a probe (shown with the probe housing removed) for use in the system shown in FIG. 1, in which the conductor partially extends around the electrode;

FIG. 4 is a cross sectional view of yet another embodiment of a probe (shown with the probe housing removed) for use in the system shown in FIG. 1, in which the electrode and conductor are both contoured to conform with a surface from which a biopotential measurement is desired;

FIG. 5 is a cross sectional view of another embodiment of a probe (shown with the probe housing removed) for use in the system shown in FIG. 1, in which the probe includes a plurality of electrodes;

DESCRIPTION OF THE PREFERRED EMBODIMENTS

Figure 6:
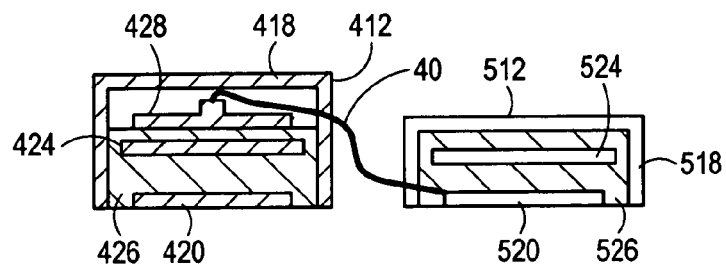
FIG. 6 is a cross sectional view of yet another embodiment of a probe for use in the system shown in FIG. 1, in which the probe electronics are shared with a secondary probe.

Referring initially to FIG. 1, a sensor system for measuring a biopotential signal is shown and generally designated 11. As shown in FIG. 1, the sensor system 11 includes a probe 12 that can be positioned adjacent to a biopotential source, in this case a patient 14. Although a human patient 14 is shown, it is to be appreciated that the sensor system 11 can be used to measure a biopotential signal from healthy humans, animals or other bodies that generate a biopotential signal. If desired, the probe 12 can receive the biopotential signal through the clothing of the patient 14, as shown in FIG. 1. In one implementation, the probe 12 is attached to or formed as an integral part of a piece of clothing that can be worn against the skin. For a biopotential signal having a frequency, f, the clothing material preferably has an electrical resistivity, $\rho$, and dielectric constant, $\in$ wherein $\rho < 5/(2\pi f \in)$. For the embodiment shown in FIG. 1, the biopotential signal is measured relative to the potential of the patient 14, which is input into the sensor system 11 via the body strap 16.

A more detailed appreciation of an embodiment of a probe 12 for use in the sensor system 11 can be had with reference to FIG. 2. As shown there, the probe 12 includes a probe housing 18 which holds an electrode 20. The electrode 20, which is typically made of a conductive metal, is provided to sense a biopotential signal from a biopotential source, such as the patient 14 shown in FIG. 1. Because the electrode 20 senses the potential in free space, a portion of the electrode 20 is typically prepared without any coatings with a high dielectric constant (i.e. a relative dielectric constant, $\in_r$, greater than 3). The electrode 20 defines an electrode center 21 that is typically positioned between Approximately 0.5 cm and approximately 10 m from the patient 14.

As shown in FIG. 2, an insulating coating 22 of a material such as Paralene can be applied to overlay the electrode 20 to prevent stray DC electrical currents from inadvertently flowing into the sensor system 11 via the electrode 20.

Continuing with FIG. 2, it can be seen that the probe 12 includes a conductor 24 that is spaced from the electrode 20. As further shown, a material 26 having relatively low electrical conductivity and dielectric constant is interposed between the conductor 24 and electrode 20 to minimize the electrical coupling between the conductor 24 and electrode 20. As detailed further below, the potential of the conductor 24 can be controlled using feedback from the measured potential of the electrode 20. The potential of the conductor 24 can be controlled to optimize the measurement SNR of the sensor system 11 and to shield the electrode 20 from electromagnetic noise from environmental sources and noise from the remainder of the sensor system 11. In one implementation, the potential of the conductor 24 is held to be substantially equal to the measured potential of the electrode 20 to serve as a guard surface for the electrode 20. Alternatively, the conductor 24 can be held at another potential to optimize some other aspect of the sensor system 11.

With continued reference to FIG. 2, it can be seen that the probe 12 also includes probe electronics 28. For the sensor system 11, the probe electronics 28 includes a high impedance first stage amplifier, and may include filtering and gain stages, batteries to provide power, and components to transmit the signal over wired/wireless links or to store the data for later output. For the probe 12 shown in FIG. 2, the probe electronics 28 and electrode 20 are located on opposite sides of the conductor 24. The spacing between the conductor 24 and probe electronics 28 is generally made as small as possible in order to minimize the overall size of the probe 12. The probe housing 18 can also function as an electromagnetic shield in addition to its function as a mechanical housing. As such, the probe housing 18 can be made of a conducting material such as a metal, or if electromagnetic shielding is not required, the probe housing 18 can be made of an insulating material. Alternatively, the probe housing 18 can be made of a composite structure having conducting and non-conducting materials.

In use, as best appreciated by cross-referencing FIGS. 1 and 2, the probe 12 can be held or mounted on the patient 14 to position the electrode 20 directly against the patient 14, against the clothing of the patient 14 or at any desired distance from the patient 14 that allows an adequate SNR in an acceptable measurement time. For example, for measuring a signal from the heart, the electrode 20 may be located up to a meter from the patient 14. Typically, the electrode 20 is located within several centimeters (i.e. about three centimeters) of the surface of the patient 14. The electrode 20 couples capacitively to the biopotential source (i.e. patient 14) and serves as the element that introduces the signal into the high impedance first stage amplifier in the probe electronics 28 via a short connector 30. For the case where the electrode 20 is immersed in a uniform electric field, the electrical potential of the electrode 20 will be equal to the free space potential at the geometric center of the electrode 20 multiplied by the impedance dividing network formed by the self capacitance of the electrode 20 and the input impedance of the first stage amplifier in the probe electronics 28.

The high impedance first stage amplifier performs an impedance transformation function and sends the resulting signal to second stage electronics 32 via connector 34. As shown in FIG. 1, the second stage electronics 32 can be located remotely from the probe 12 and can provide functions such as additional amplification, filtering, analog to digital conversion, and wireless transmission of data. As further shown, the probe electronics 28 are electrically connected to the conductor 24 via connector 36 allowing the potential of the conductor 24 to be controlled as described above. The sensor system 11 may also include a capacitive or inductive interface (not shown) to provide stimulation signals to the biopotential source or related parts of the biopotential source. Alternatively, this interface may be provided as a separate, stand-alone system.

FIG. 3 shows another embodiment of a probe (designated probe 112) for use in the sensor system 11 having an electrode 120, conductor 124 and probe electronics 128. The probe electronics 128 are electrically connected to the conductor 124 allowing the potential of the conductor 124 to be controlled as described above. As shown, for the probe 112, the conductor 124 is formed with extensions 38a,b which extend around the electrode 120. As further shown, a material 126 having a relatively low electrical conductivity and dielectric constant is interposed between the conductor 124 and electrode 120 to minimize the electrical coupling between the conductor 124 and electrode 120.

FIG. 4 shows an embodiment of a probe (designated probe 212) for use in the sensor system 11 having an electrode 220, conductor 224 and probe electronics 228. As shown, for the probe 212, the electrode 220 and conductor 224 are parallel and contoured to follow the shape of the surface of the region to be measured. If desired, the probe electronics 228 may also be contoured. As further shown, a material 226 having a relatively low electrical conductivity and dielectric constant is interposed between the conductor 224 and electrode 220 to minimize the electrical coupling between the conductor 224 and electrode 220. For the probe 212, the materials used to construct the electrode 220 and conductor 224 may be flexible, or rigid materials can be fabricated to the desired contour.

The compact, three dimensional design of the probes 12, 112, 212 minimizes probe size allowing a number of practical advances, such as allowing a high density of probes 12, 112, 212 to be used. The small probe size also provides improved comfort for a wearable implementation. Further, the probes 12, 112, 212 can be positioned side by side, as is the case for conventional skin contacting electrodes, or in any position relative to each other.

FIG. 5 shows an embodiment of a probe (designated probe 312) for use in the sensor system 11 having electrodes 320a and 320b, conductors 324a, 324b and 324c and probe electronics 328. As shown, the electrodes 320a and 320b are arranged to measure the electric potential at two different stand-off distances from the biopotential source. The potential of each electrode 320a,b can be measured independently using two separate channels of electronics and provided as separate outputs, or the difference in potentials can be taken using a differential first stage amplifier and only the difference outputted. In a further embodiment, both the individual potentials and the differential potential can be provided. In addition, the conductors 324a, 324b and 324c can be driven to pre-selected potentials to maximize the measurement SNR or reduce sensor size. As further shown in FIG. 5, a material 326 having a relatively low electrical conductivity and dielectric constant is interposed between the conductors 324a–c and electrodes 320a,b to minimize the electrical coupling between the conductors 324a–c and electrodes 320a,b.

FIG. 6 shows an embodiment of a probe (designated probe 412) for use in the sensor system 11 that is electrically connected to a secondary probe 512. As shown, the probe 412 includes a probe housing 418 and has an electrode 420, conductor 424 and probe electronics 428. Also shown, the secondary probe 512 includes a probe housing 518 and has an electrode 520 and conductor 524 that are electrically connected to the probe electronics 428 of the probe 412 using a well shielded connector 40. The connector 40 may include a separate shielding layer that functions as a guard to minimize the capacitance to ground of the signal part of the connector 40. Thus, the probe electronics 428 receive separate inputs from electrode 420 and electrode 520. The potential of each electrode 420, 520 can be measured independently using two separate channels of electronics and provided as separate outputs, or the difference in potentials can be taken using a differential first stage amplifier and only the difference outputted. In a further embodiment, both the individual potentials and the differential potential can be provided. In addition, the conductors 424, 524 can be driven to pre-selected potentials to maximize the measurement SNR or reduce sensor size. Also shown in FIG. 6, a material 426 having relatively low electrical conductivity and dielectric constant is interposed between the conductor 424 and electrode 420 to minimize the electrical coupling between the conductor 424 and electrode 420. Similarly, a material 526 having relatively low electrical conductivity and dielectric constant is interposed between the conductor 524 and electrode 520 to minimize the electrical coupling between the conductor 524 and electrode 520. Although FIG. 6 shows only one secondary probe 512 electrically connected to probe 412, it is to be appreciated by those skilled in the pertinent art that as many secondary probes 512 as desired can be electrically connected to the probe electronics 428 of probe 412.

Figure 7:
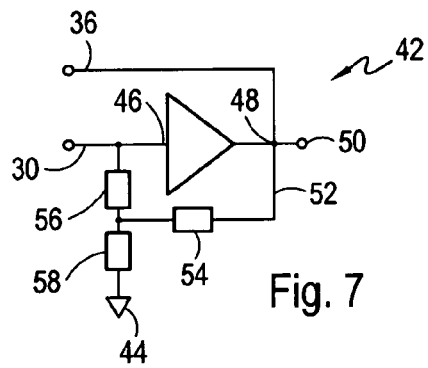
FIG. 7 is a schematic diagram of a high impedance first stage amplifier for use in a system for measuring a biopotential signal.

FIG. 7 shows an embodiment of a high impedance first stage amplifier (designated 42) for use in the probe electronics 28, 128, 228 of the probes 12, 112, 212 shown in FIGS. 2–4 to perform an impedance transformation from the electrode 20, 120, 220 to the second stage electronics 32 (see FIG. 1). For the FIG. 7 embodiment, the high impedance first stage amplifier 42 is a unity gain amplifier with the measurement made relative to circuit ground 44. Cross-referencing FIGS. 2 and 7, it can be seen that electrode 20 is connected to the high impedance first stage amplifier 42 via connector 30 and conductor 24 is connected to the high impedance first stage amplifier 42 via connector 36.

In greater detail, it can be seen that the high impedance first stage amplifier 42 has an input port 46 and a guard 48 of a type that is known to the skilled artisan. The guard 48 provides a voltage that can be used to minimize leakage of the signal to the environment during passage to the input port 46 of the amplifier 42. Preferably, the input port 46 and the guard 48 will have substantially the same input potential.

In accordance with the normal operation of the amplifier 42, the amplifier 42 receives an input signal; amplifies the input signal by a gain, G; and then provides the amplified input signal as an output 50 to second stage electronics 32 via connector 34 (See FIG. 1). However, the input signal is received from an electrode 20, 120, 220 having an ultrahigh impedance which can disrupt the normal operation of an amplifier 42. As is well known in the pertinent art, for the amplifier 42 to be operationally effective, the input impedance of the amplifier 42 needs to be matched to the input impedance of the electrode 20, 120, 220. When an ultrahigh impedance is involved, however, the input bias current that is inherently generated by an amplifier 42 can cause a rapid saturation of the amplifier 42. The input potential at both the input port 46 and the guard 48 will be the same, and it will include both the input signal (an a.c. signal) and the input bias current of the amplifier 42 (essentially a d.c. signal). The solution, then, is to somehow remove the input bias current from the input potential at the input port 46.

Still referring to FIG. 7, for one embodiment of the present invention, the amplifier 42 includes a guard line 52, which interconnects the guard 48 with an electronic device 54. For the amplifier 42, the device 54 is preferably a capacitor having a capacitance. The device 54 may, however, be a filter. In either case, the purpose of the device 54 is to isolate the input bias current (i.e. d.c. signal or very low frequency signal) and separate it from the input signal that is taken from the guard 48. Recall, the input potential at the guard 48, and at the input port 46, includes both the input signal and the input bias current. The result is that the device 54 creates a corrective signal which is essentially the a.c. input signal. Further, for this embodiment of the present invention, another electronic device 56 is interconnected between the device 54 and the connector 30 that is used to feed the input signal to the input port 46. The device 56 is preferably a diode of a type well known in the pertinent art. Specifically, the device 56 (diode) is connected so that the input potential at the input port 46 will interact with the corrective signal from the device 54 (i.e. the input signal). The diode of device 56 is connected to present a very high impedance to ground 44 at the input port 46. Conduction through device 56 (diode) occurs via the leakage current of the device 56. This leakage current may be very small (e.g. a few pA). Alternatively the device 56 can be a resistor of value sufficiently high to minimize conduction of the signal away from the input port 46 due to imbalance in the potentials of the guard 48 and input line connector 30. The purpose here is for this interaction to block the input signal from passing through the device 56. On the other hand, the concerted operation of the devices 54 and 56 allows the input bias current in the input potential to pass through the device 56 and through a resistor 58 to ground 44. Consequently, the input bias current is removed from the input potential at the input port 46.

Figure 8:
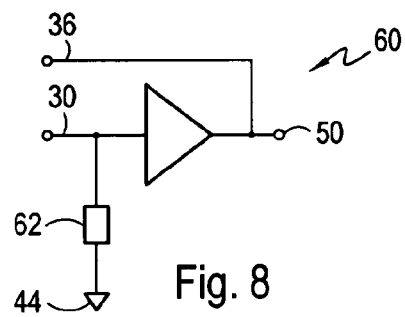
FIG. 8 is a schematic diagram of another embodiment of a high impedance first stage amplifier for use in a system for measuring a biopotential signal.

FIG. 8 shows another embodiment of a high impedance first stage amplifier (designated 60) for use in the probe electronics 28, 128, 228 of the probes 12, 112, 212 shown in FIGS. 2–4 to perform an impedance transformation from the electrode 20, 120, 220 to the second stage electronics 32 (see FIG. 1). Amplifier 60 is similar to the amplifier 42 shown in FIG. 7 with the exception that the device 54 has been removed and the device 56 and resistor 58 have been combined as a pure resistive element 62. High impedance first stage amplifiers 42 and 60 can be used in probe electronics 28, 128, 228 of respective probes 12, 112, 212 or two such high impedance first stage amplifiers 42 and 60 can be used in probe electronics 328, 428 of respective probes 312, 412.

Figure 9:
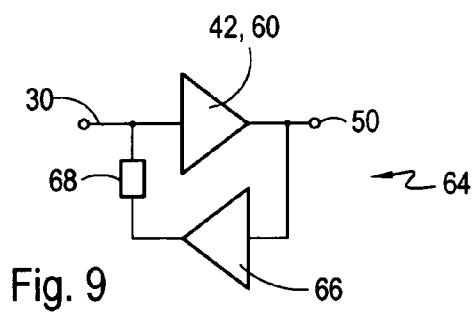
FIG. 9 is a schematic diagram of yet another embodiment of a high impedance first stage amplifier for use in a system for measuring a biopotential signal.

FIG. 9 shows another embodiment of a high impedance first stage amplifier (designated 64) for use in the probe electronics 28, 128, 228, 328, 428 of respective probes 12, 112, 212, 312, 412 shown in FIGS. 2–6 to perform an impedance transformation from the electrodes 20, 120, 220, 320a,b, 420, 520 to the second stage electronics 32 (see FIG. 1). As shown, a feedback circuit containing an amplifier 66 and a capacitor 68 is used to implement a negative capacitance function that eliminates or reduces the input capacitance of the input amplifier 42, 60 which can be either the high impedance first stage amplifier 42 shown in FIG. 7 or the high impedance first stage amplifier 60 shown in FIG. 8.

Figure 10:
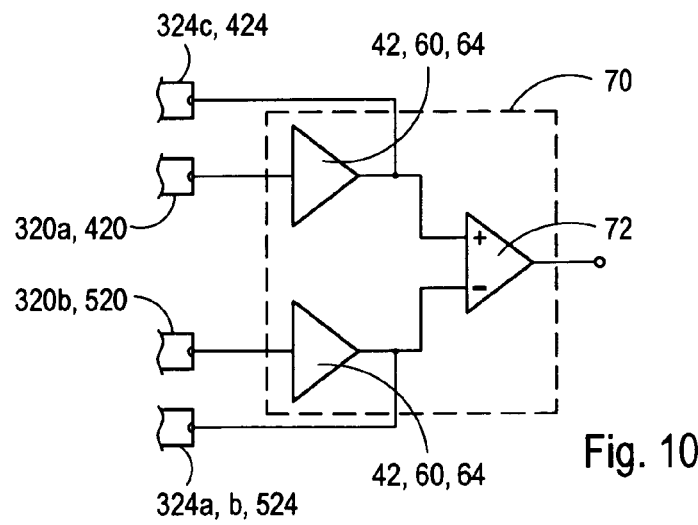
FIG. 10 is a schematic diagram of yet another embodiment of a high impedance first stage amplifier for use in a system for measuring a biopotential signal.

FIG. 10 shows another embodiment of a high impedance first stage amplifier (designated 70) for use in the probe electronics 328, 428 of respective probes 312, 412 shown in FIGS. 5 and 6 to perform an impedance transformation from either electrodes 320a,b or electrodes 420, 520 to the second stage electronics 32 (see FIG. 1). When used in probe electronics 328, the high impedance first stage amplifier 70 measures the signal from electrode 320a relative to electrode 320b without direct reference to a circuit ground and controls the potential of conductors 324a–c as shown. Similarly, when used in probe electronics 428, the high impedance first stage amplifier 70 measures the signal from electrode 420 relative to electrode 520 without direct reference to a circuit ground and controls the potential of conductor 424 and conductor 524, as shown. Also shown, the high impedance first stage amplifier 70 includes a differential amplifier 72 and two amplifiers 42, 60, 64, each of which can be either the high impedance first stage amplifier 42 shown in FIG. 7, the high impedance first stage amplifier 60 shown in FIG. 8 or the high impedance first stage amplifier 64 shown in FIG. 9. For the sensor system 11, the high impedance first stage amplifiers 42, 60, 64 and 70 can be constructed from operational amplifiers, discrete transistors, or a pre-packaged instrumentation amplifier.

Figure 11:
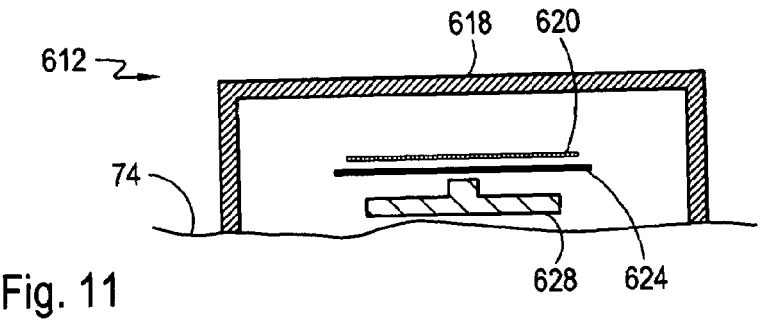
FIG. 11 is a cross sectional view of another embodiment of a probe for use in the system shown in FIG. 1, in which the conductor is positioned for placement between the electrode and the biopotential signal source and the probe electronics are positioned inside the probe housing.

FIG. 11 shows an embodiment of a probe (designated probe 612) for use in the sensor system 11 that includes a probe housing 618 and has an electrode 620, conductor 624 and probe electronics 628. FIG. 11 shows the probe housing 618 positioned against a surface 74 which is typically a patient's skin or clothing. As shown, for the probe 612, the conductor 624 is positioned for placement between the electrode 620 and the surface 74, and the probe electronics 628 are positioned inside the probe housing 618 to interpose the conductor 624 between the electrode 620 and probe electronics 628. For the system 11, the conductor 624 can be driven to a pre-selected potential to maximize the measurement SNR or reduce sensor size. The probe 612 positions the electrode 620 at a distance from the surface 74 and reduces artifact signals that would be caused if the electrode 620 was placed against the surface 74 and held with pressure. The mutual capacitance between the electrode 620 and surface 74 is reduced, and in some cases eliminated by the conductor 624, allowing the electrode 620 to sense only the free space potential.

Figure 12:
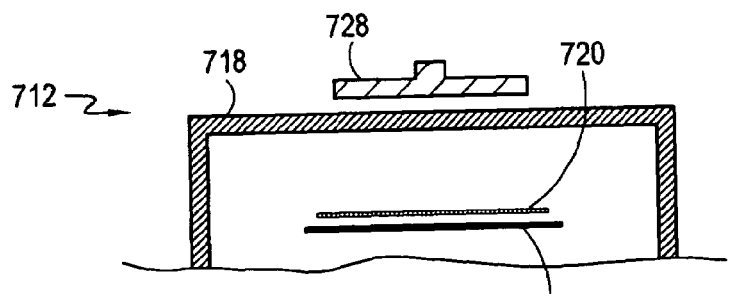
FIG. 12 is a cross sectional view of still another embodiment of a probe for use in the system shown in FIG. 1, in which the conductor is positioned for placement between the electrode and biopotential signal source and the probe electronics are positioned outside the probe housing.

FIG. 12 shows an embodiment of a probe (designated probe 712) for use in the sensor system 11 that includes a probe housing 718 and has an electrode 720, conductor 724 and probe electronics 728. The probe 712 shown in FIG. 12 is somewhat similar to the probe 612 shown in FIG. 11 except the probe electronics 728 are positioned outside the probe housing 718.

Figure 13:
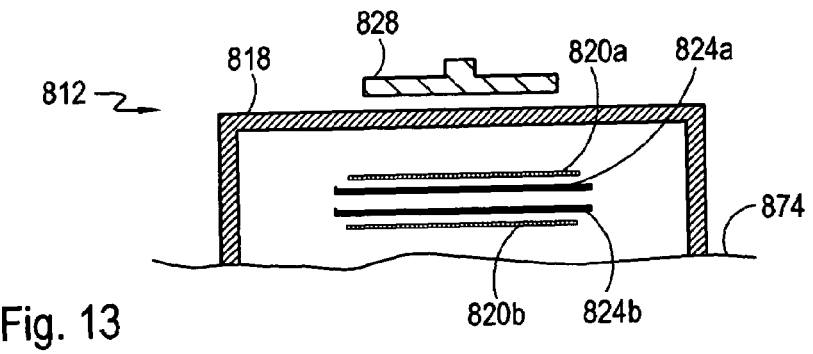
FIG. 13 is a cross sectional view of yet another embodiment of a probe for use in the system shown in FIG. 1 having a pair of conductors that are interposed between a pair of electrodes and in which the probe electronics are positioned inside the probe housing.

FIG. 13 shows an embodiment of a probe (designated probe 812) for use in the sensor system 11 that includes a probe housing 818 and has electrodes 820a,b, conductors 824a,b and probe electronics 828. As shown, for the probe 812, the conductors 824a,b are interposed between electrodes 820a,b and the probe electronics 828 are positioned outside the probe housing 818. For the system 11, the conductors 824a,b can be driven to pre-selected potentials to maximize the measurement SNR or reduce sensor size. The probe 812 distances the electrodes 820a,b from the surface 874 and reduces artifact signals that would be caused if one of the electrodes 820a,b was placed against the surface 874 and held with pressure. The mutual capacitance between the electrodes 820a,b and surface 874 is reduced, and in some cases eliminated by the conductor 824, allowing the electrode 820 to sense only the free space potential. The probe electronics 828 receive separate inputs from electrode 820a and electrode 820b. The potential of each electrode 820a,b can be measured independently using two separate channels of electronics and provided as separate outputs, or the difference in potentials can be taken using a differential first stage amplifier and only the difference outputted. In a further embodiment, both the individual potentials and the differential potential can be provided.

Figure 14:
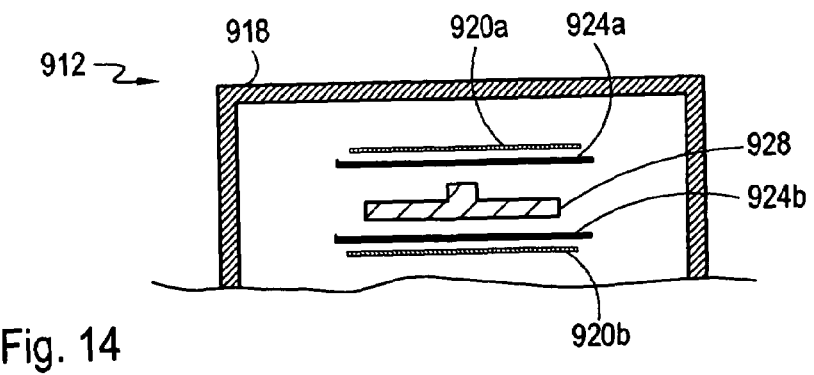
FIG. 14 is a cross sectional view of another embodiment of a probe for use in the system shown in FIG. 1 having a pair of conductors that are interposed between a pair of electrodes and in which the probe electronics are positioned outside the probe housing.

FIG. 14 shows an embodiment of a probe (designated probe 912) for use in the sensor system 11 that includes a probe housing 918 and has electrodes 920a,b, conductors 924a,b and probe electronics 928. The probe 912 shown in FIG. 14 is somewhat similar to the probe 812 shown in FIG. 13 except the probe electronics 928 are positioned between the conductors 924a,b in the probe housing 918.

While the particular sensor system for measuring biopotentials as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for measuring a biopotential signal produced by a body in free space, said system comprising:
   an electrode made of a conducting material, said electrode being positionable at a location adjacent the body to place said electrode at a first potential;
   a conductor located at a fixed distance from said electrode;
   a means for generating a reference potential; and
   a high impedance amplifier connected to said reference potential generating means, with said amplifier having an input port electrically connected to said electrode to compare said first electrical potential of said electrode with said reference potential to generate a signal indicative of the biopotential signal, and wherein said conductor is located to shield said electrode from electrical noise wherein said conductor is interposed between said electrode and said amplifier to shield said electrode from electric signals of said amplifier.

2. A system as recited in claim 1 further comprising a means for mounting said electrode on the body.

3. A system as recited in claim 1 wherein said electrode is a first electrode and said means for generating a reference potential comprises a second electrode and said system further comprises a means for coupling said first electrode with said second electrode for movement therewith.

4. A system as recited in claim 1 wherein said electrode is a first electrode and said means for generating a reference potential comprises a second electrode that is placed in electrical contact with the body.

5. A system as recited in claim 1 wherein said means for generating a reference potential comprises a wire that is electrically connected to a local ground.

6. A system as recited in claim 1 further comprising a means for placing said conductor at a predetermined potential to shield said electrode from electrical signals of said amplifier.

7. A system as recited in claim 6 wherein said predetermined potential is substantially equal to said first electrical potential.

8. A system as recited in claim 1 wherein said high impedance amplifier comprises an instrumentation amplifier.

9. A system as recited in claim 1 wherein said high impedance amplifier comprises an operational amplifier.

10. A system as recited in claim 1 wherein said high impedance amplifier comprises at least one transistor.

11. A system as recited in claim 1 wherein said electrode is formed with a surface and at least a portion of said surface is coated with a resistive coating to shield said electrode from stray electrical currents.

12. A system as recited in claim 1 wherein said system further comprises a low-conductivity material interposed between said electrode and said conductor to minimize electrical coupling between said electrode and said conductor.

13. A system as recited in claim 1 wherein said amplifier is positioned to interpose said electrode between said body and said amplifier.

14. A system as recited in claim 1 wherein said electrode is attached to a material that can be worn against the skin.

15. A system as recited in claim 14 wherein said biopotential signal has a frequency, f, said material has an electrical resistivity, $\rho$, and dielectric constant, $\in$ and wherein $\rho < 5/(2\pi f \in)$.

16. A system for measuring a biopotential signal produced by a body in free space, said system comprising:
   an electrode made of a conducting material, said electrode being positionable at a location adjacent the body to place said electrode at a first potential;
   a conductor located at a fixed distance from said electrode;
   a means for generating a reference potential; and
   a high impedance amplifier connected to said reference potential generating means, with said amplifier having an input port electrically connected to said electrode to compare said first electrical potential of said electrode with said reference potential to generate a signal indicative of the biopotential signal, and wherein said conductor is located to shield said electrode from electrical noise wherein said conductor is adapted to be interposed between said electrode and said body.

17. A system for measuring a biopotential signal at a location adjacent to a patient, said system comprising:
   means for generating a reference electrical potential;
   a probe having an electrode positionable at said location to place said electrode at a first electrical potential, a conductor spaced from said electrode, and a highimpedance amplifier positioned to interpose said conductor between said amplifier and said electrode, said amplifier electrically connected to said generating means and said electrode to compare said first electrical potential to said reference electrical potential and generate a signal that is indicative of the biopotential signal in response thereto; and
   means for controlling the electrical potential of said conductor to shield said electrode from electrical noise.

18. A system as recited in claim 17 wherein said electrode is a first electrode and said means for generating a reference electrical potential comprises a second electrode that is incorporated in said probe.

19. A system as recited in claim 17 wherein said electrode is a first electrode and said means for generating a reference electrical potential comprises a second electrode that is placed in electrical contact with the patient.

20. A method for measuring a biopotential signal at a location adjacent to a patient, said method comprising the steps of:
   providing an electrode made of a conductive material;
   maintaining a conductor spaced at a fixed distance from said electrode;
   controlling the electrical potential of said conductor to shield said electrode from electrical noise;
   coupling a high impedance amplifier to said electrode for movement therewith;
   positioning said electrode at said location to place said electrode at a first electrical potential;
   placing the conductor between the electrode and said high impedance amplifier;
   generating a reference electrical potential;
   inputting said first electrical potential and said reference electrical potential into said high impedance amplifier; and
   using said high impedance amplifier to compare said first electrical potential to said reference electrical potential and generate an output signal that is indicative of the biopotential signal in response thereto.

21. A method as recited in claim 20 wherein said electrode is positioned at said location to interpose at least one article of clothing between said electrode and said patient.

22. A method as recited in claim 20 wherein said electrode is a first electrode and said step of generating a reference electrical potential comprises the step of coupling a second electrode to said first electrode for movement therewith, said second electrode being spaced from said first electrode to generate a second electrical potential.

23. A method as recited in claim 20 wherein said electrode is a first electrode and said step of generating a reference electrical potential comprises the step of contacting the patient with a second electrode to generate a second electrical potential.

24. A method as recited in claim 20 wherein said steps of generating a reference electrical potential and inputting said first electrical potential and said reference electrical potential into said high impedance amplifier comprises the step of connecting said high impedance amplifier to ground.

25. A method as recited in claim 20 wherein said step of controlling the electrical potential of said conductor to shield said electrode from electrical noise is accomplished using feedback generated by said high impedance amplifier.

26. A method as recited in claim 25 wherein said electrical potential of said conductor is held substantially equal to the electrical potential of said electrode.

27. A method as recited in claim 20 wherein said electrode defines an electrode center and said positioning step places said electrode center between approximately 0.5 cm and approximately 10 m from said patient.

28. A method as recited in claim 20 wherein said electrode defines an electrode center and is formed with a surface and said positioning step places said electrode center at said location and places said surface in contact with said patient.

29. A probe for measuring a biopotential signal produced by a body in free space comprising:
a first electrode made of a conducting material, the first electrode being adapted to be positioned adjacent the body to place the first electrode at a first potential;
a first conductor spaced from the first electrode;
system electronics for reviewing input from the first electrode located near the first electrode and separated from the first electrode by the first conductor; and
a material having a relatively low electrical conductivity and dielectric constant interposed between the first conductor and the first electrode thus minimizing electrical coupling between the first conductor and the first electrode.

30. The probe as recited in claim 29 further comprising, in combination, a second electrode made of a conducting material and a second conductor spaced from said second electrode, said second electrode being positionable, separate from said first electrode, at a location adjacent the body to place the second electrode at a second potential whereby the system electronics receive input from the second electrode.

31. The probe as recited in claim 29 further comprising: a housing, wherein the first electrode is adapted to be located closer to the body than the first conductor and the system electronics are located outside the housing.

32. The probe as recited in claim 29 further comprising: a second electrode made of a conducting material spaced from the first electrode, and a second conductor spaced from the first electrode, the second conductor being located between the second electrode and the first conductor whereby the system electronics receive input from the second electrode.

33. The probe as recited in claim 29, further comprising: a conducting housing establishing an environmental noise shield, said conducting housing enclosing the first electrode, the first conductor and the system electronics, while maintaining exposure of a probe side portion for measuring the biopotential signal.

34. The probe as recited in claim 32 wherein the first electrode, the first conductor, the second electrode and the second conductor are arranged in a stacked configuration.

35. The probe as recited in claim 32 further comprising: a third conductor located at a fixed distance from the first electrode and being located between the system electronics and the second electrode.

36. The probe as recited in claim 32 wherein said system electronics are located a fixed distance from the first electrode so as to be located farther away from the body than each of the first and second conductors and the first and second electrodes.

37. The probe as recited in claim 32 wherein said system electronics are located between the first and second conductors.

38. The probe as recited in claim 37 further comprising: a housing surrounding the first and second electrodes, first and second conductors and the electronics.

39. The probe as recited in claim 32 further comprising: a housing, wherein the system electronics are located outside the housing, the second electrode is located between the first electrode and the housing, and the first and second conductors are located at fixed distances from the first electrode, between the first electrode and the second electrode and within the housing.

40. The probe as recited in claim 32 wherein the system electronics are adapted to be located further away from the body than each of the first electrode and the first conductor, the second electrode is adapted to be located further away from the body than the system electronics, and the second conductor is located between the system electronics and the second electrode.

\* \* \* \* \*

UNITED STATES PATENT AND TRADEMARK OFFICE
CERTIFICATE OF CORRECTION

PATENT NO. : 6,961,601 B2  Page 1 of 1
DATED : November 1, 2005
INVENTOR(S) : Matthews et al.

It is certified that error appears in the above-identified patent and that said Letters Patent is hereby corrected as shown below:

<u>Column 1,</u>
Lines 12-13, insert the following paragraph:
--               Statement of Government Interest The U.S. Government has a paid-up license in this
invention and the right in limited circumstances to
require the patent owner to license others on
reasonable terms as provided for by the terms of DARPA
Contract Nos. DAAH01-03-C-R041 and DAAH01-03-C-R290. --.

Signed and Sealed this

Fourth Day of April, 2006

JON W. DUDAS
*Director of the United States Patent and Trademark Office*